(12) United States Patent
Wu et al.

(10) Patent No.: US 8,976,929 B2
(45) Date of Patent: Mar. 10, 2015

(54) AUTOMATIC GENERATION OF PATIENT-SPECIFIC RADIATION THERAPY PLANNING PARAMETERS

(75) Inventors: Qingrong Jackie Wu, Chapel Hill, NC (US); Yaorong Ge, Winston-Salem, NC (US); Fang-Fang Yin, Chapel Hill, NC (US); Xiaofeng Zhu, Morrisville, NC (US)

(73) Assignee: Duke University, Durham, NC (US)

( * ) Notice: Subject to any disclaimer, the term of this patent is extended or adjusted under 35 U.S.C. 154(b) by 444 days.

(21) Appl. No.: 13/184,746

(22) Filed: Jul. 18, 2011

(65) Prior Publication Data

US 2012/0014507 A1     Jan. 19, 2012

Related U.S. Application Data

(60) Provisional application No. 61/365,105, filed on Jul. 16, 2010.

(51) Int. Cl.
*A61N 5/10* (2006.01)
*H05G 1/26* (2006.01)
*A61B 6/03* (2006.01)

(52) U.S. Cl.
CPC ........... *A61N 5/10* (2013.01); *A61N 2005/1041* (2013.01)
USPC ............................... 378/65; 378/91; 378/165

(58) Field of Classification Search
CPC ...... A61B 6/00; A61B 6/5211; A61B 6/5217; A61N 5/00; A61N 5/10; A61N 5/103; A61N 5/1031; A61N 5/1037; A61N 5/1048; A61N 5/1049; A61N 5/1064; A61N 5/1071; A61N 5/1075

USPC .............. 378/4–20, 65, 68, 69, 91, 162–165, 378/204, 205, 210, 901; 600/425–429; 250/370.01, 370.07, 370.08, 370.09, 250/371, 491.1, 526
See application file for complete search history.

(56) References Cited

U.S. PATENT DOCUMENTS

| | | | |
|---|---|---|---|
| 6,430,307 B1 * | 8/2002 | Souma et al. | 382/118 |
| 6,882,702 B2 * | 4/2005 | Luo | 378/65 |
| 7,027,557 B2 * | 4/2006 | Llacer | 378/65 |
| 7,298,819 B2 * | 11/2007 | Dooley et al. | 378/65 |
| 7,362,848 B2 * | 4/2008 | Saracen et al. | 378/65 |
| 7,590,219 B2 * | 9/2009 | Maurer et al. | 378/65 |
| 7,693,257 B2 * | 4/2010 | Allison | 378/65 |
| 2006/0274885 A1 * | 12/2006 | Wang et al. | 378/65 |

(Continued)

*Primary Examiner* — Anastasia Midkiff
(74) *Attorney, Agent, or Firm* — Kaplan Breyer Schwarz & Ottesen, LLC

(57) ABSTRACT

An apparatus and method for automatically generating radiation treatment planning parameters are disclosed. In accordance with the illustrative embodiment, a database is constructed that stores: (i) patient data and past treatment plans by expert human planners for these patients, and (ii) optimal treatment plans that are generated using multi-objective optimization and Pareto front search and that represent the best tradeoff opportunities of the patient case, and a predictive model (e.g., a neural network, a decision tree, a support vector machine [SVM], etc.) is then trained via a learning algorithm on a plurality of input/output mappings derived from the contents of the database. During training, the predictive model is trained to identify and infer patterns in the treatment plan data through a process of generalization. Once trained, the predictive model can then be used to automatically generate radiation treatment planning parameters for new patients.

18 Claims, 18 Drawing Sheets

(56) References Cited

U.S. PATENT DOCUMENTS

2008/0008291 A1* 1/2008 Alakuijala et al. .............. 378/65
2009/0295756 A1* 12/2009 Shamaie ....................... 345/175
2011/0153547 A1* 6/2011 McNutt et al. ................. 706/54

* cited by examiner

AUTOMATIC GENERATION OF PATIENT-SPECIFIC RADIATION THERAPY PLANNING PARAMETERS

CROSS REFERENCE TO RELATED APPLICATIONS

This application claims the benefit of U.S. Provisional Patent Application No. 61/365,105, filed Jul. 16, 2010, entitled "Automatic Generation of Patient-Specific IMRT Planning Parameters By Learning From Prior Plans," which is also incorporated by reference.

FIELD OF THE INVENTION

The present invention relates to cancer radiation therapy, and, more particularly, to an automated method of generating patient-specific planning parameters for radiation therapy.

BACKGROUND OF THE INVENTION

Radiation therapy, or radiotherapy, is the medical use of ionizing radiation to control malignant cells. In intensity-modulated radiation therapy (IMRT), the intensity or segment of the radiation is modified in accordance with a treatment plan to deliver highly conformal radiation doses to the patient target volume (PTV) of malignant cells, while sparing the surrounding organs at risk (OARs) and other healthy tissues from radiation damage. By dividing the PTV and OAR volumes into individual volume elements (or "voxels"), the IMRT treatment plan can be characterized by a three dimensional dose distribution that characterizes the magnitude of radiation at each of the voxels. An effective two dimensional representation of the dose distribution is the dose volume histogram (DVH).

The development of an intensity-modulated radiation therapy (IMRT) treatment plan (or simply "IMRT planning") typically involves a complex optimization procedure by which the radiation beam angles and strengths are designed to achieve required dose of radiation for the patient target volume, as well as limit the radiation delivered to neighboring normal tissues as prescribed. While a portion of the IMRT planning process may be performed via computerized optimization algorithms, typically much of the process requires the input and expertise of a human planner.

In particular, the human planner is typically responsible for manually adjusting planning dose objectives (e.g., dose limits, dose volume histogram [DVH] limits, etc.) via a time-consuming, iterative trial-and-error process. The trial-and-error nature of the process is due to the fact that the planner does not know whether or not a set of given dose objectives will result in a plan that meets all physician-prescribed goals for sparing organs at risk (known as "sparing goals"), or when it does, whether tradeoffs between patient target volume (PTV) coverage and sparing of organs at risk (OARs) can be further improved.

Further compounding the process is the fact that physician-prescribed sparing goals are often adapted from clinical trial studies for general populations (e.g., the Radiation Therapy Oncology Group's (RTOG) sparing goals, the QUANTEC (Quantitative Analysis of Normal Tissue Effects in the Clinic) toxicity data, etc.) that ignore specific anatomical, geometric, and demographic information for individual patients, and often represent the upper limit of an organ's dose tolerance rather than an individual patient's lowest achievable dose in that organ. Moreover, because of the lack of quantitative tools for linking variations in anatomy to variations in OAR sparing doses, planners must rely on personal experience and expertise when making adjustments for individual patients.

What is needed, therefore, is a method of predicting intensity-modulated radiation therapy (IMRT) treatment planning parameters that account for anatomical and other variations between patients, without relying entirely on human planner judgment.

SUMMARY OF THE INVENTION

The present invention comprises an apparatus and method for the automated generation of radiation treatment planning parameters. In accordance with the illustrative embodiment, a database of training treatment plans is constructed that stores patient data and one or both of:

(i) past treatment plans by expert human planners for these patients, and (ii) optimal treatment plans that are generated using multi-objective optimization and Pareto front search, and that represent the best tradeoff opportunities of the patient case, and a predictive model (e.g., a neural network, a decision tree, a support vector machine [SVM], a statistical regression, etc.) is then trained via a learning algorithm on a plurality of input/output mappings derived from the contents of the database.

In accordance with the illustrative embodiment, each input/output mapping corresponds to a particular patient, where the input comprises features that include:

(i) data based on a geometric (linear or non-linear) characterization of one or more organs at risk proximate to the patient's target volume, as well as a characterization of the patient's target volume in relation to one or more of these organs;

(ii) the size (i.e., volume) and shape of the patient's target volume, and (iii) the size(s) and shape(s) of the organ(s) at risk, which includes partial portions of interest (e.g., an overlap portion with target, a portion outside the primary radiation field, etc.);

(iv) the sparing characteristics of organ(s) at risk (e.g., serial versus parallel risk type, the significant volume size for toxicity risk factors, etc.);

(v) other patient specific features such as clinical and demographic variables; and (vi) machine specific features such as the treatment modality and beam angle arrangement;

and where the output comprises data based on achieved dose distributions for the patient (e.g., three-dimensional dose distributions, dose volume histograms, etc.) that were extracted from training treatment plans.

In accordance with the illustrative embodiment, an effective method for characterizing the geometry of one organ at risk in relation to the target volume(s) is the distance to target histogram (DTH). This histogram measures the portion of OAR volume that is at a certain distance from the target volume, and vice versa. The distance in DTH may be measured in Euclidean space or in some other non-Euclidean space, in a linear or non-linear manner (e.g., a distance space distorted by the radiation beam geometry or dose deposition characteristics, etc.). The DTH is a two-dimensional representation of the three-dimensional geometry relating one structure (organ or target) to another structure (organ or target).

During training, the predictive model is trained to identify and infer patterns in the treatment plan data through a process of generalization. Once trained, the predictive model can then be used to automatically generate radiation treatment planning parameters for new patients. These planning parameters may include dose distributions, dose volume histograms, beam configurations, and so forth.

The illustrated embodiment comprises: receiving by a data-processing system one or more data, wherein at least one of the data is based on a geometric characterization of one or more organs at risk proximate to a target volume of a patient P; and generating by the data-processing system one or more radiation treatment planning parameters for the patient P based on the one or more data.

DETAILED DESCRIPTION

Figure 1:
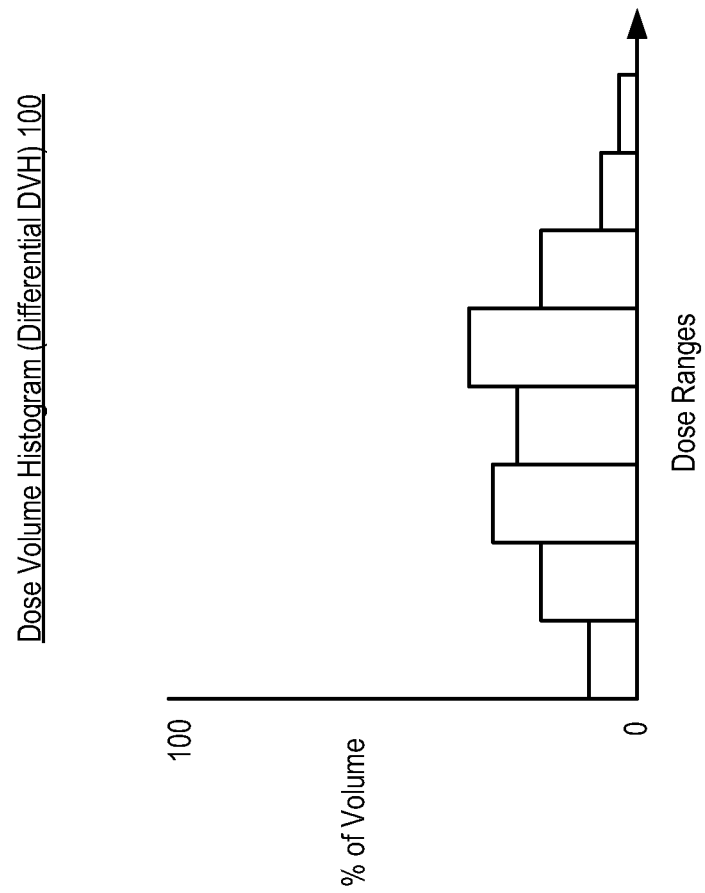
FIG. 1 depicts a first illustrative dose volume histogram, in accordance with the illustrative embodiment of the present invention.

FIG. 1 depicts first illustrative dose volume histogram (DVH) 100, referred to as a "differential DVH," in accordance with the illustrative embodiment of the present invention. As shown in FIG. 1, DVH 100 associates each of a plurality of dosage ranges (e.g., 0-2 Gy, 2-4 Gy, etc.) inside the volume of an organ at risk (x-axis) with the percentage of the volume being exposed to that dosage range (y-axis). As will be appreciated by those skilled in the art, in some embodiments of the present invention dose volume histogram 100 might be derived from a dose distribution, while in some other embodiments dose volume histogram 100 might be derived from dose volume histogram 200, described below and with respect to FIG. 2, while in still some other embodiments dose volume histogram 100 might be derived from some other data or obtained in some other manner.

Figure 2:
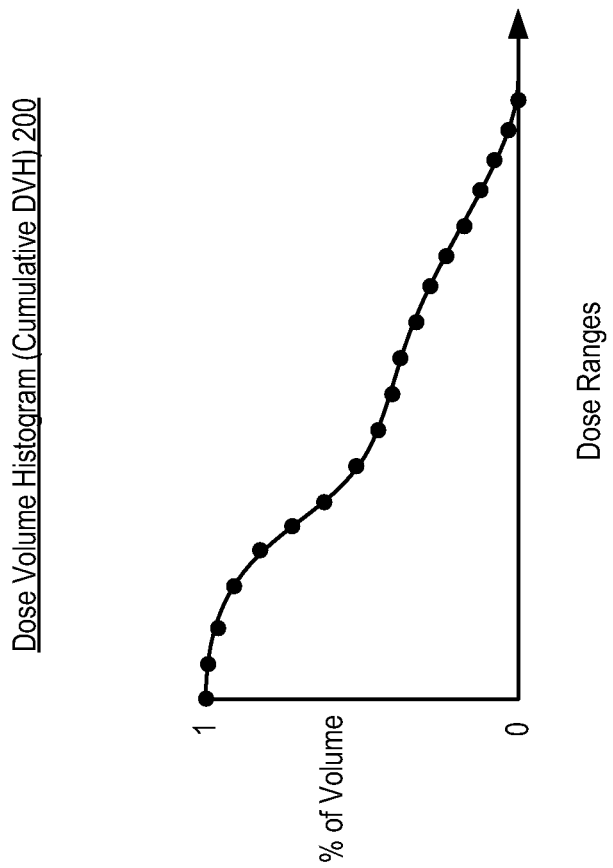
FIG. 2 depicts a second illustrative dose volume histogram, in accordance with the illustrative embodiment of the present invention.

FIG. 2 depicts second illustrative dose volume histogram (DVH) 200, referred to as a "cumulative DVH," in accordance with the illustrative embodiment of the present invention. As shown in FIG. 2, DVH 200 associates dosage range (x-axis) with the percentage of an organ or target volume (y-axis, where 1 corresponds to 100% volume and 0 corresponds to 0% volume). As will be appreciated by those skilled in the art, in some embodiments of the present invention dose volume histogram 200 might be derived from dose volume histogram 100, while in some other embodiments dose volume histogram 200 might be derived directly from a dose distribution, while in still some other embodiments dose volume histogram 200 might be derived from some other data or obtained in some other manner.

Figure 3:
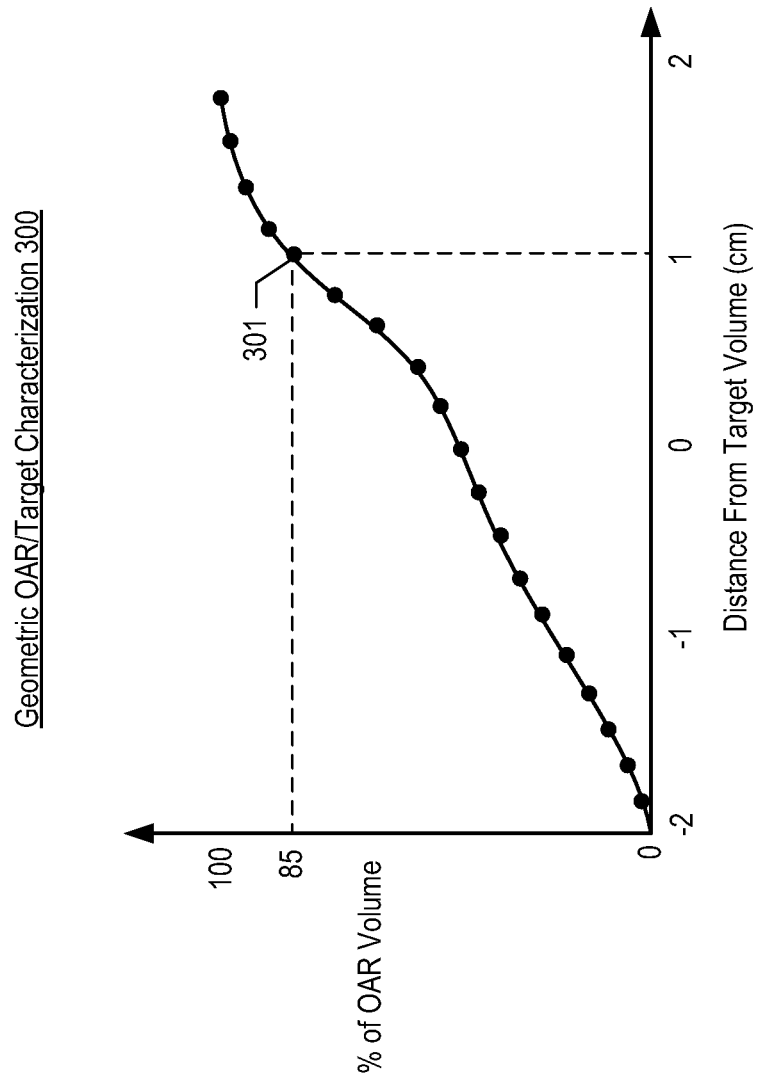
FIG. 3 depicts an illustrative distance to target histogram characterizing the geometry of one or more organs at risk (OAR) with respect to a target volume, in accordance with the illustrative embodiment of the present invention.

FIG. 3 depicts illustrative graph 300 characterizing the geometry of one or more organs at risk (OAR) with respect to a target volume, in accordance with the illustrative embodiment of the present invention. As shown in FIG. 3, graph 300 associates distance from the target volume (x-axis) with a percentage of the total volume of the organ(s) at risk (y-axis), where a negative distance indicates overlap between the target and OAR. For example, point 301 indicates that 85% of the total volume of the organ(s) at risk is within one centimeter of the target volume. The distance can be further defined as linear or nonlinear, using Euclidean or other non-Euclidean metric space.

Figure 4:
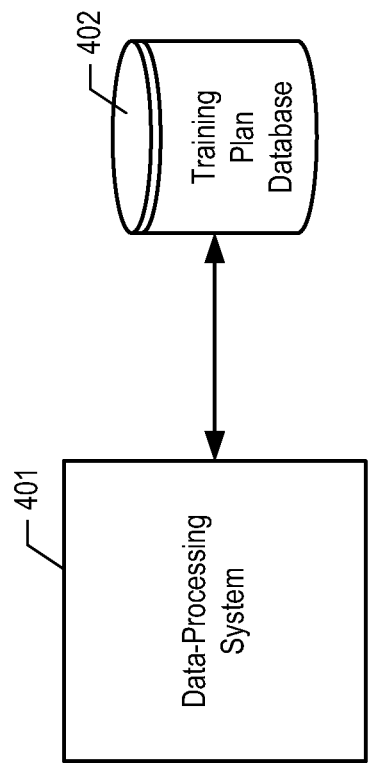
FIG. 4 depicts the salient elements of automated planning parameter-generation system 400, in accordance with the illustrative embodiment of the present invention.

FIG. 4 depicts the salient elements of automated planning parameter-generation system 400, in accordance with the illustrative embodiment of the present invention. As shown in FIG. 4, automated planning parameter-generation system 400 comprises data-processing system 401 and training plan database 402, interconnected as shown.

Data-processing system 401 is an apparatus comprising hardware and software (e.g., a server, a desktop computer, a notebook computer, etc.) that is capable of reading from and writing to training plan database 402, of storing a representation of a predictive model, of training the predictive model, of generating a computer-executable program that applies the trained predictive model, and of executing the tasks described below and with respect to FIGS. 11 through 15. Data-processing system 401 is described in detail below and with respect to FIG. 5.

Training plan database 402 is capable of providing persistent storage of data and efficient retrieval of the stored data, in well-known fashion. The contents of plan database are described in detail below and with respect to FIGS. 6 through 10.

Figure 5:
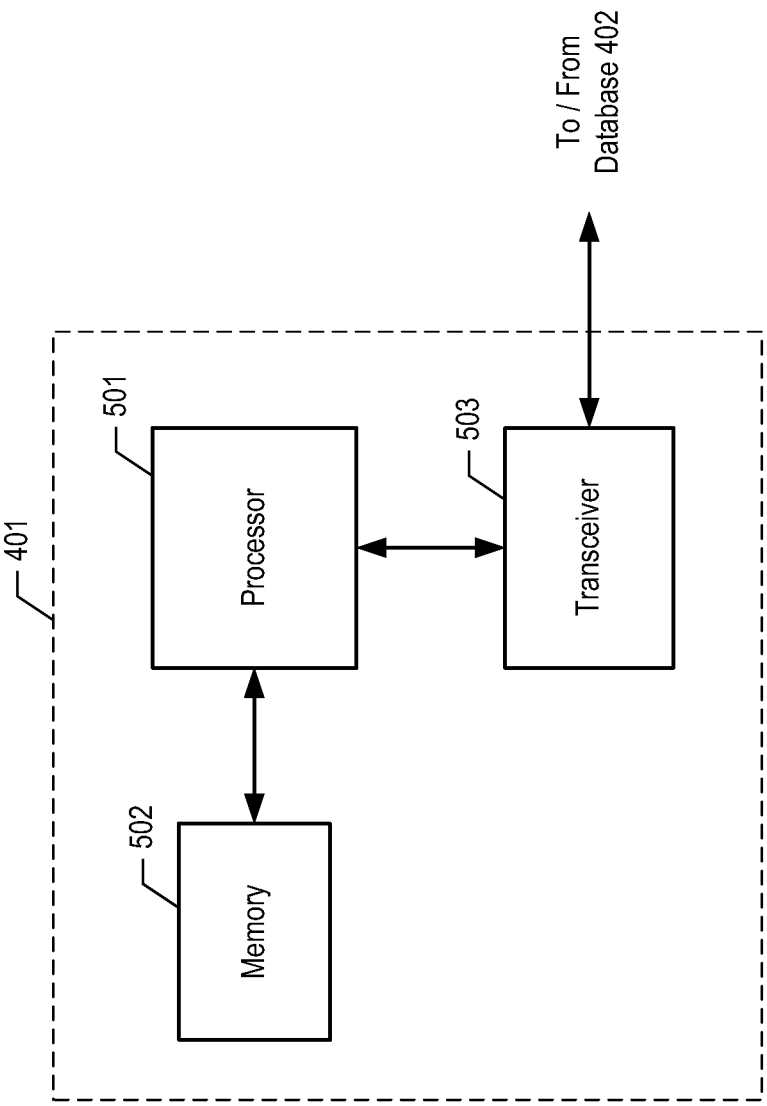
FIG. 5 depicts a block diagram of the salient elements of data-processing system 401, as shown in FIG. 4, in accordance with the illustrative embodiment of the present invention.

FIG. 5 depicts a block diagram of the salient elements of data-processing system 401, in accordance with the illustrative embodiment of the present invention. As shown in FIG. 5, data-processing system 401 comprises processor 501, memory 502, and transceiver 503, interconnected as shown.

Processor 501 is a general-purpose processor that is capable of receiving information from transceiver 503, of reading data from and writing data into memory 502, of executing instructions stored in memory 502, and of forwarding information to transceiver 503, in well-known fashion. As will be appreciated by those skilled in the art, in some alternative embodiments of the present invention processor 501 might be a special-purpose processor, rather than a general-purpose processor.

Memory 502 is capable of storing data and executable instructions, in well-known fashion, and might be any combination of random-access memory (RAM), flash memory, disk drive, etc. In accordance with the illustrative embodiment, memory 502 stores executable instructions corresponding to the tasks of the methods of FIGS. 11 through 15 below.

Transceiver 503 is capable of receiving signals from plan database 402 and forwarding information encoded in these signals to processor 501, and of receiving information from processor 501 and transmitting signals that encode this information to plan database 402, in well-known fashion.

Figure 6:
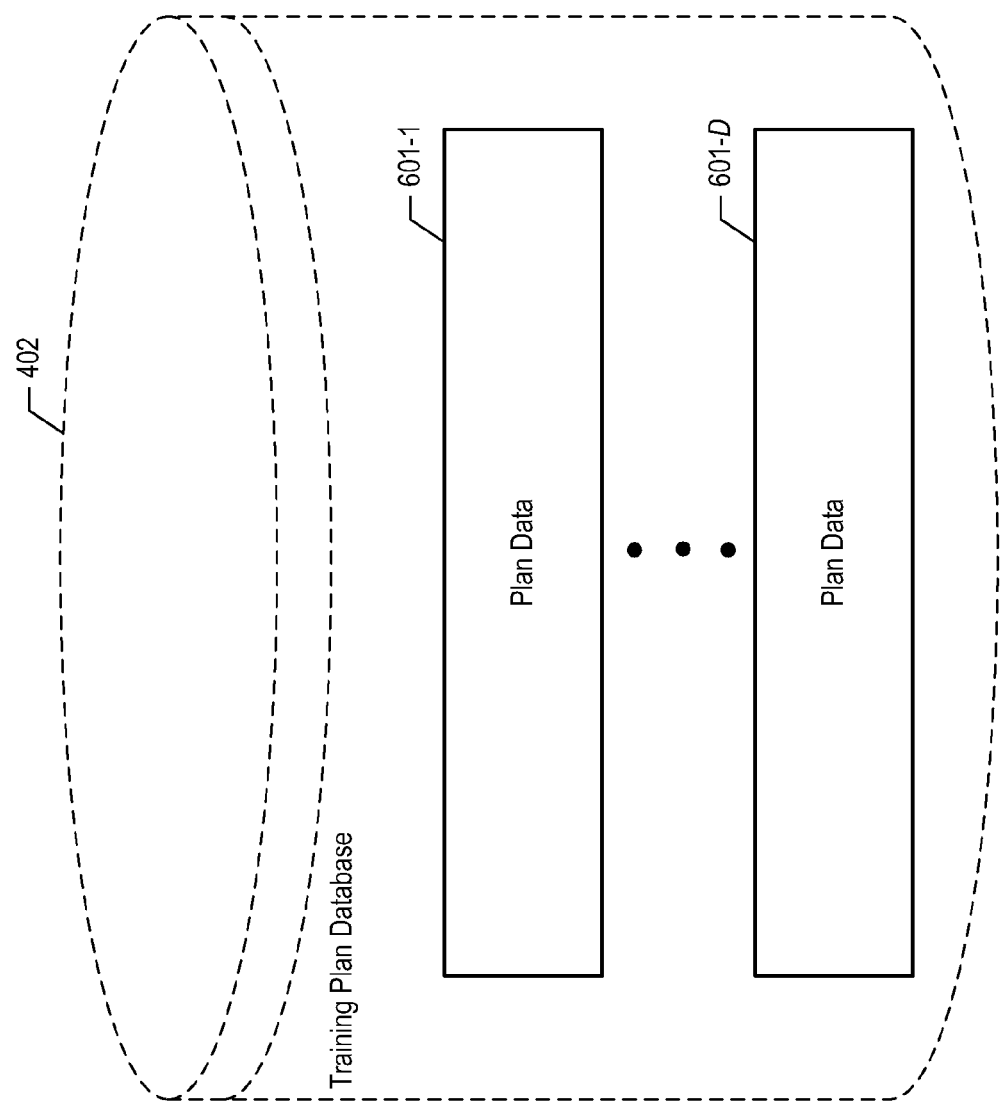
FIG. 6 depicts a block diagram of the salient data stored in plan database 402, as shown in FIG. 4, in accordance with the illustrative embodiment of the present invention.

FIG. 6 depicts a block diagram of the salient data stored in plan database 402, in accordance with the illustrative embodiment of the present invention. As shown in FIG. 6, plan database comprises records 601-1 through 601-D, where each record 601-$i$ corresponds to a respective patient and contains data associated with a training treatment plan that was formulated by an expert human planner for the patient using either a trial-and-error approach or a pareto-front guided search process. The contents of record 601-$i$ are described in detail below and with respect to FIGS. 7 through 10.

Figure 7:
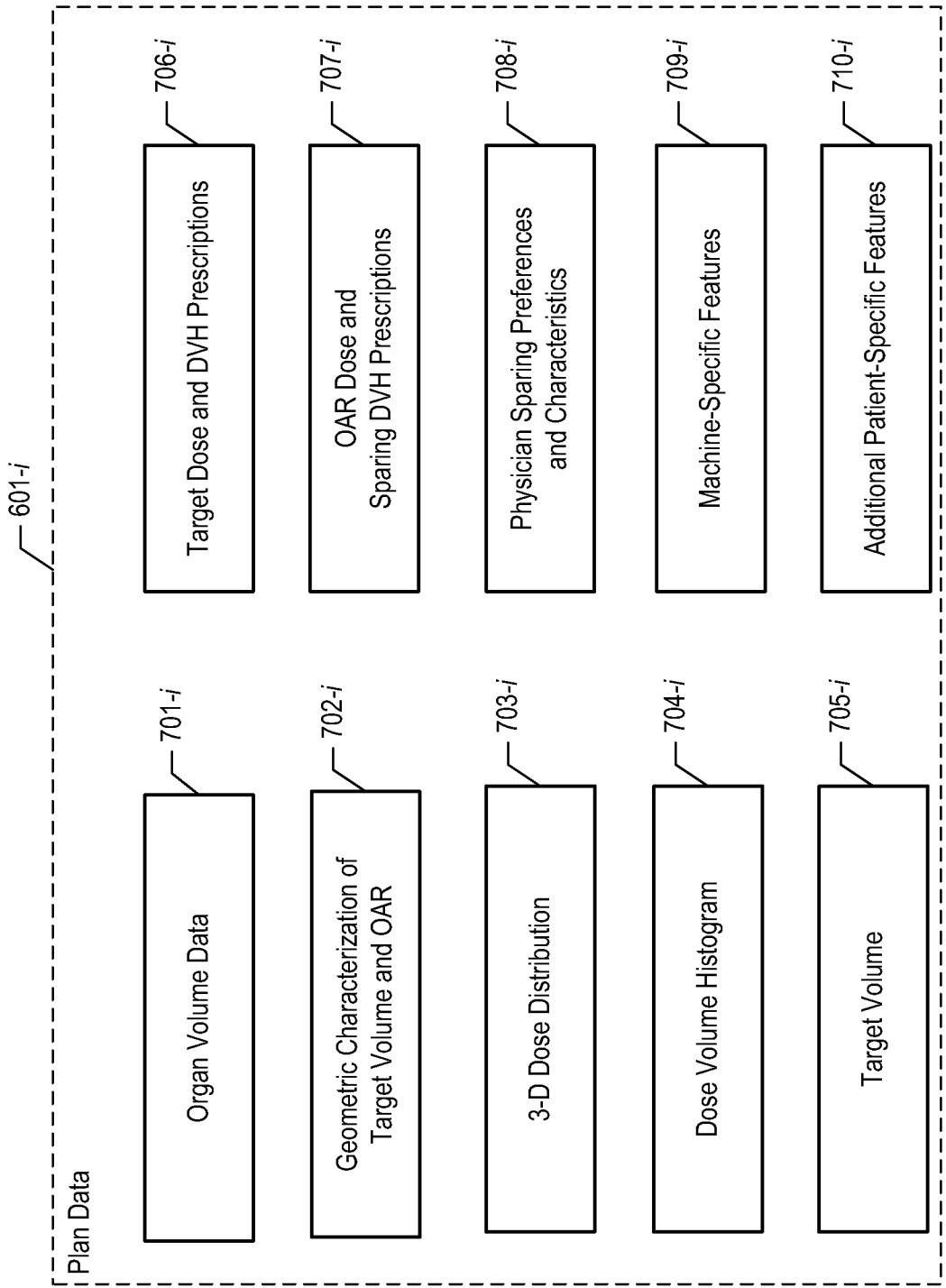
FIG. 7 depicts a block diagram of the contents of plan data 601-*i*, as shown in FIG. 6, in accordance with the illustrative embodiment of the present invention.

FIG. 7 depicts a block diagram of the contents of record 601-$i$, where i is an integer between 1 and D inclusive, in accordance with the illustrative embodiment of the present invention. As shown in FIG. 7, record 601-$i$ comprises: organ volume data 701-$i$, which is further described below and with respect to FIG. 8; geometric characterization 702-$i$, which is further described below and with respect to FIG. 9; three-dimensional dose distribution 703-$i$; dose volume histogram 703-$i$, which is further described below and with respect to FIG. 10; target volume 705-$i$; target dose and DVH prescriptions 706-$i$; OAR dose and DVH sparing prescriptions 707-$i$; physician sparing preferences and characteristics 708-$i$ (e.g., limit lung volume receiving at least 10 Gy to less than 5%, meet all sparing goals for single-kidney patient, etc.); machine-specific features 709-$i$ (e.g., treatment modality, beam angle arrangement, etc.); and additional patient-specific features 710-$i$ (e.g., clinical variables, demographic variables, etc.).

Figure 8:
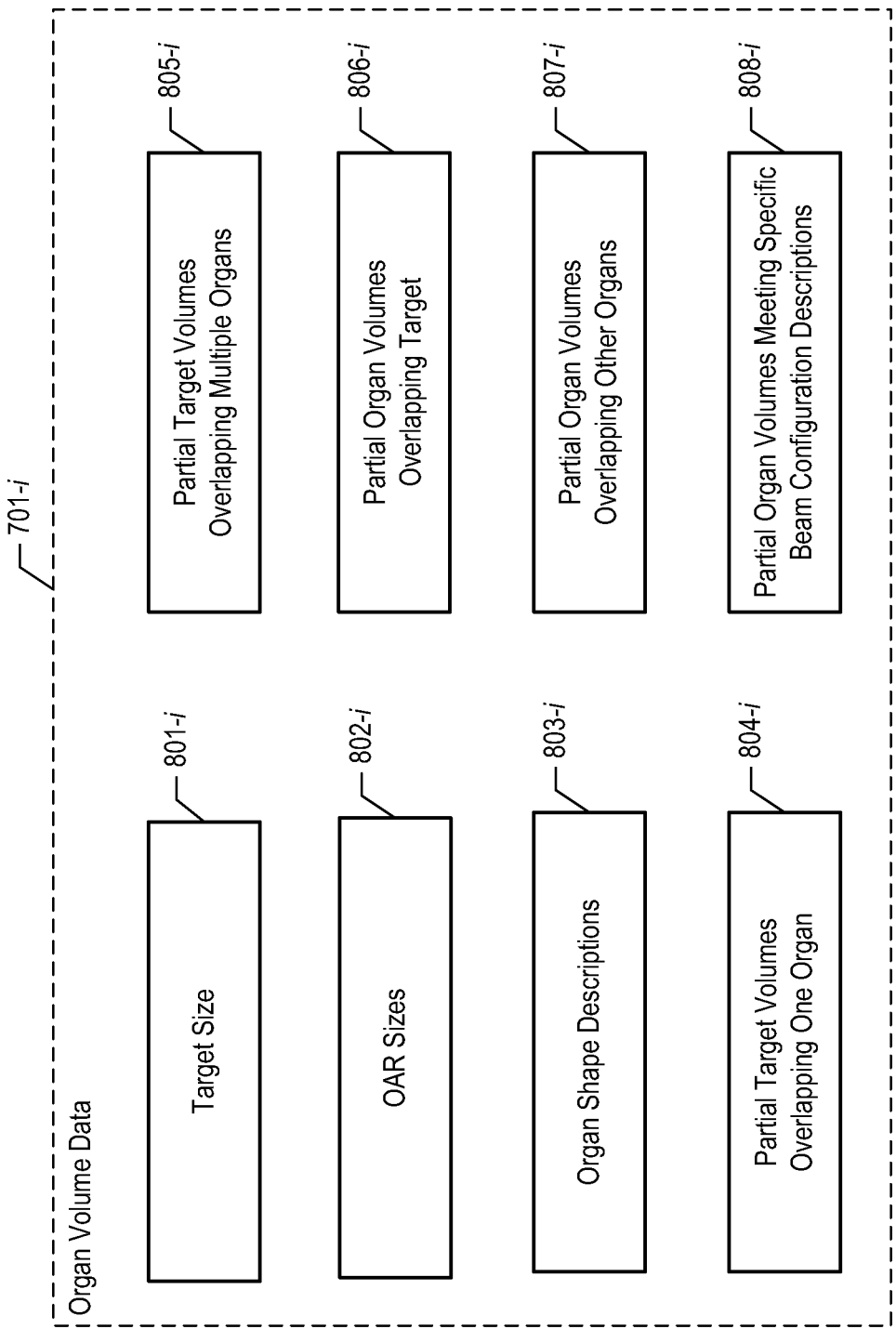
FIG. 8 depicts the contents of organ volume data 701-*i*, as shown in FIG. 7, in accordance with the illustrative embodiment of the present invention.

FIG. 8 depicts the contents of organ volume data 701-$i$, where i is an integer between 1 and D inclusive, in accordance with the illustrative embodiment of the present invention. As shown in FIG. 8, organ volume data 701-$i$ stores: target volume size 801-$i$, which is the size (i.e., volume) of the target volume, in appropriate units (e.g., cubic millimeters, etc.); organ at risk (OAR) volume sizes 802-$i$; organ shape descriptions 803-$i$; partial target volumes 804-$i$ overlapping one organ; partial target volumes 805-$i$ overlapping multiple organs; partial organ volumes 806-$i$ overlapping target; partial organ volumes 807-$i$ overlapping other organs; and partial organ volumes 808-$i$ meeting specific beam configuration descriptions (e.g., partial volumes residing outside primary radiation fields, etc.).

Figure 9:
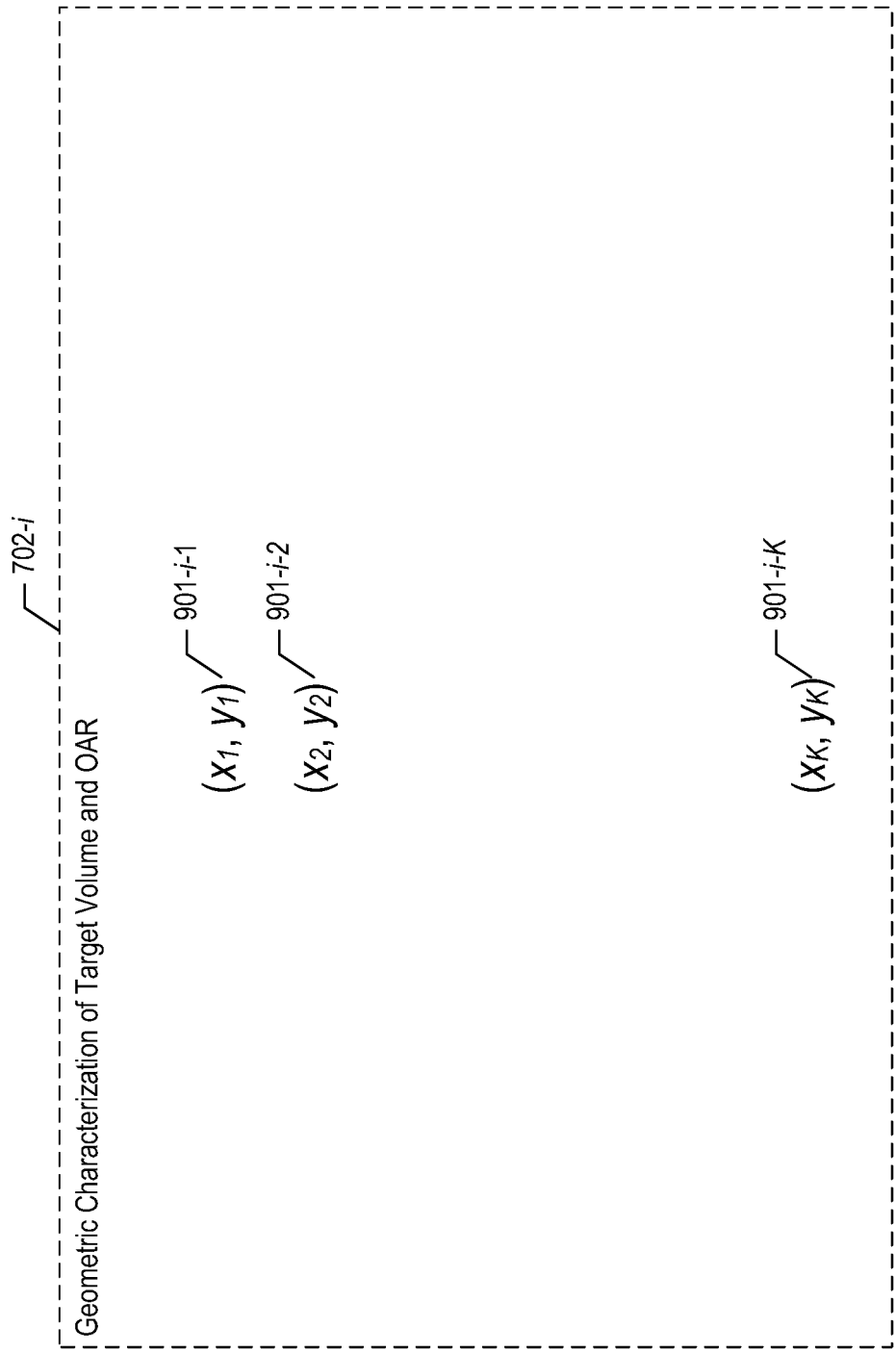
FIG. 9 depicts the contents of geometric characterization 702-*i*, as shown in FIG. 7, in accordance with the illustrative embodiment of the present invention.

FIG. 9 depicts the contents of geometric characterization 702-$i$, where i is an integer between 1 and D inclusive, in accordance with the illustrative embodiment of the present invention. As shown in FIG. 9, geometric characterization 702-$i$ comprises two-dimensional points 901-$i$-1 through 901-$i$-K, where K is a positive integer, and where each of the points associates distance from the target volume with a percentage of the total volume of the organ(s) at risk. In other words, each of points 901-$i$-1 through 901-$i$-K correspond to a point on the type of curve illustrated in FIG. 3.

As will be appreciated by those skilled in the art, geometric characterization 702-$i$ of the illustrative embodiment covers the tools and methods that can characterize the geometry of one organ at risk in relation to one or more target volumes, and to other organs at risk. One such geometry description tool is the distance to target histogram (DTH), which measures the portion of OAR or target volume that is at a certain distance from the target volume or other organs. The distance in DTH may be measured in Euclidean space or in some other non-Euclidean space, in a linear or non-linear manner (e.g., a distance space distorted by the radiation beam geometry or dose deposition characteristics, etc.).

Figure 10:
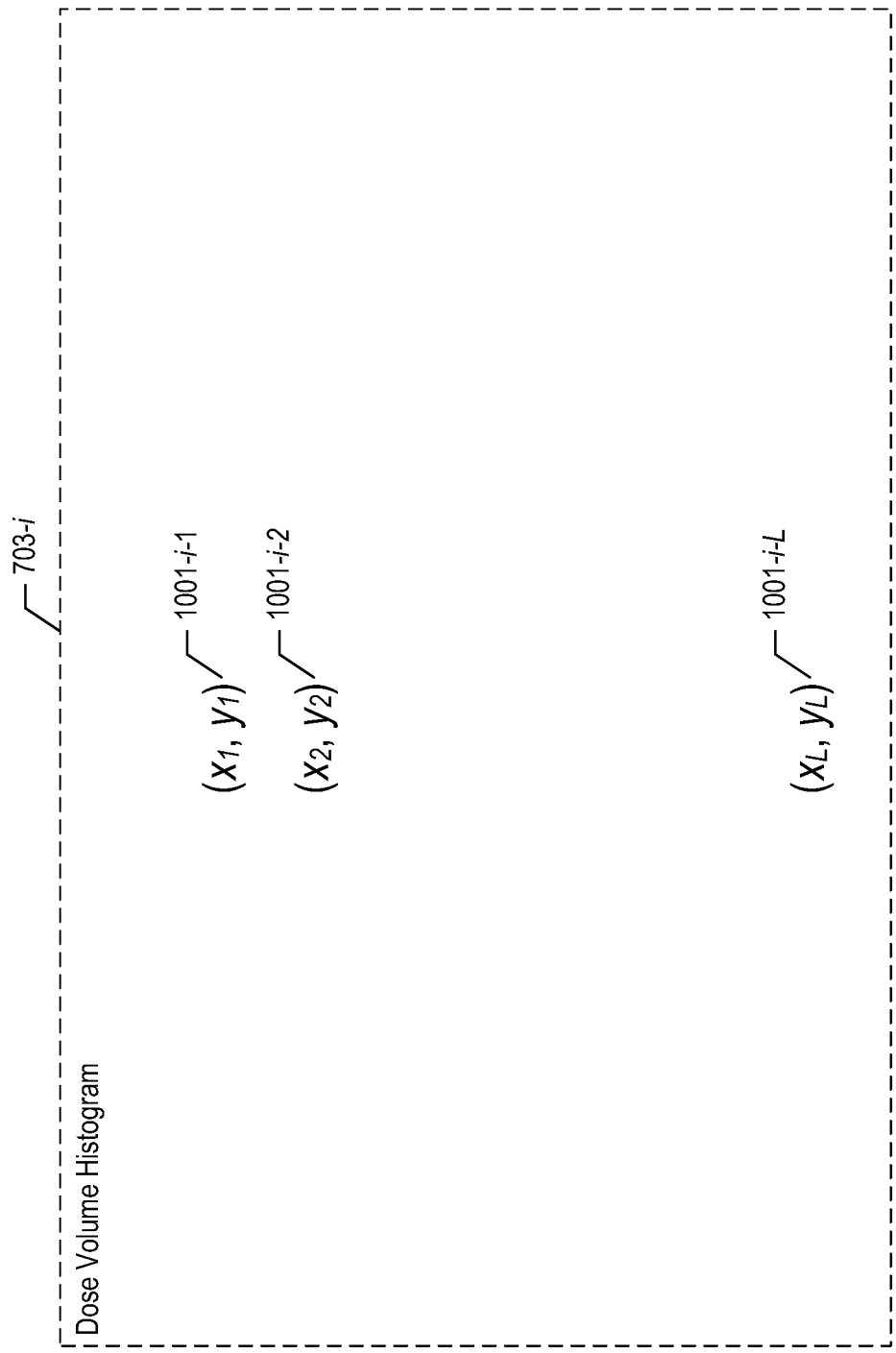
FIG. 10 depicts the contents of dose volume histogram 703-*i*, as shown in FIG. 7, in accordance with the illustrative embodiment of the present invention.

FIG. 10 depicts the contents of dose volume histogram 703-$i$, where i is an integer between 1 and D inclusive, in accordance with the illustrative embodiment of the present invention. As shown in FIG. 10, dose volume histogram 703-$i$ comprises two-dimensional points 1001-$i$-1 through 1001-$i$-L, where L is a positive integer, and where each of the points is taken from the dose volume histogram for the patient. As described above, in some embodiments of the present invention, each of points 1001-$i$-1 through 1001-$i$-L might associate dosage ranges with a percentage of the volume being exposed to that dosage range (e.g., points corresponding to the histogram bins of illustrative DVH 100 in FIG. 1, etc.), while in some other embodiments, each of points 1001-$i$-1 through 1001-$i$-L might associate dose value with a percentage of the volume being exposed to that dose or higher (e.g., points corresponding to those of illustrative DVH 200 in FIG. 2, etc.), while in still some other embodiments, each of points 1001-$i$-1 through 1001-$i$-L might be obtained from some other type of representation of the dose volume histogram for the patient.

Figure 11:
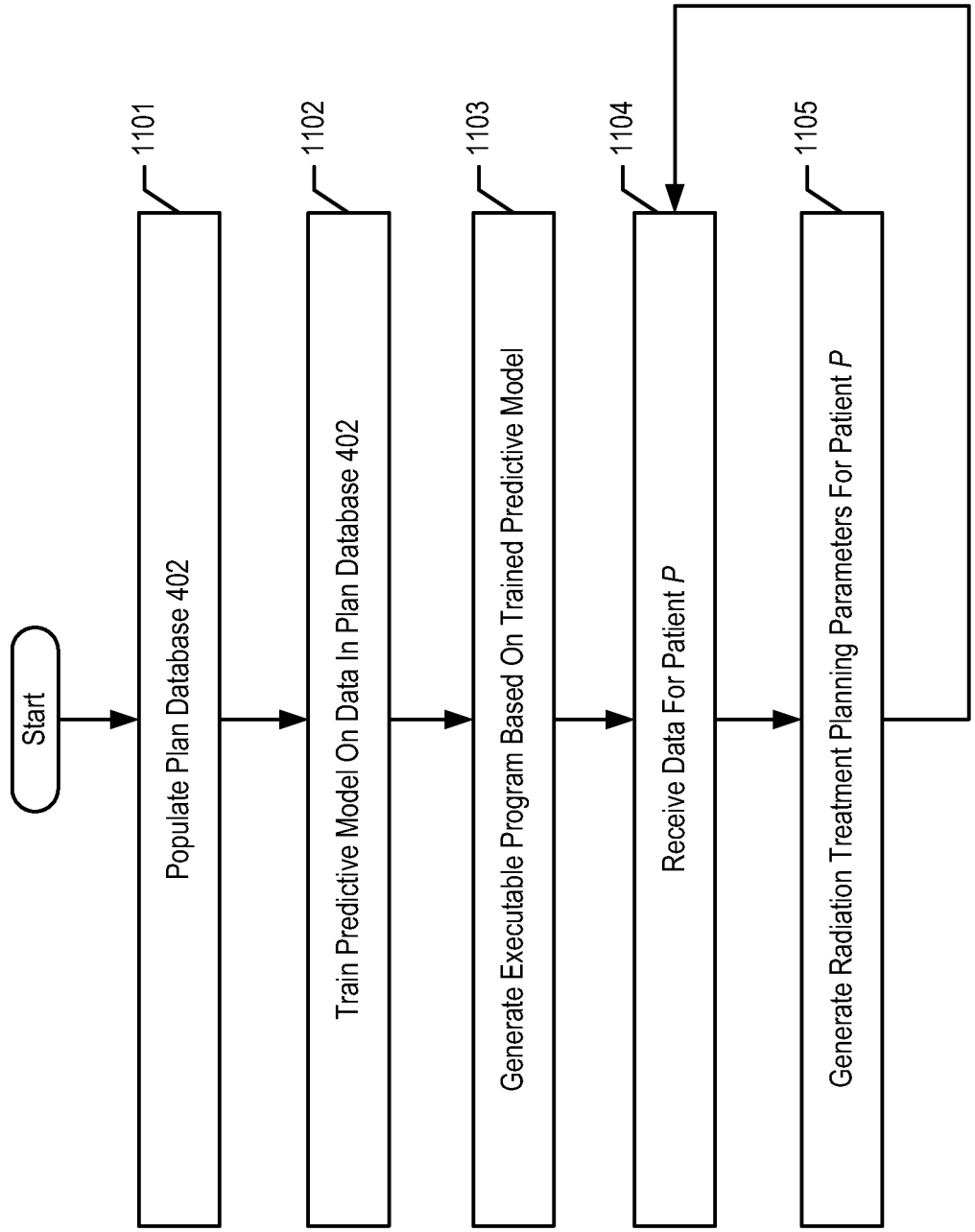
FIG. 11 depicts a flowchart of the salient tasks performed by data-processing system 401, in accordance with the illustrative embodiment of the present invention.

FIG. 11 depicts a flowchart of the salient tasks performed by data-processing system 401, in accordance with the illustrative embodiment of the present invention. It will be clear to those skilled in the art, after reading this disclosure, which tasks depicted in FIG. 11 can be performed simultaneously or in a different order than that depicted.

At task 1101, data-processing system 401 populates plan database 402. Task 1101 is described in detail below and with respect to FIG. 12.

At task 1102, data-processing system 401 trains a predictive model on the data in plan database 402. Task 1102 is described in detail below and with respect to FIG. 13.

At task 1103, data-processing system 401 generates an executable program based on the trained predictive model, in well-known fashion.

At task 1104, data-processing system 401 receives data for a patient P for whom a radiation treatment plan is desired. In accordance with the illustrative embodiment, these data include, but are not limited to:

the size and shape of patient P's target volume;
the size(s) and shape(s) of each of patient P's organ(s) at risk; and
a geometric characterization (of the form of the illustrative curve depicted in FIG. 3) of patient P's organ(s) at risk with respect to the target volume.

At task 1105, data-processing system 401 generates a set of radiation treatment planning parameters for patient P. Task 1105 is described in detail below and with respect to FIGS. 16 through 18.

After task 1105 has been completed, execution continues back at task 1104.

Figure 12:
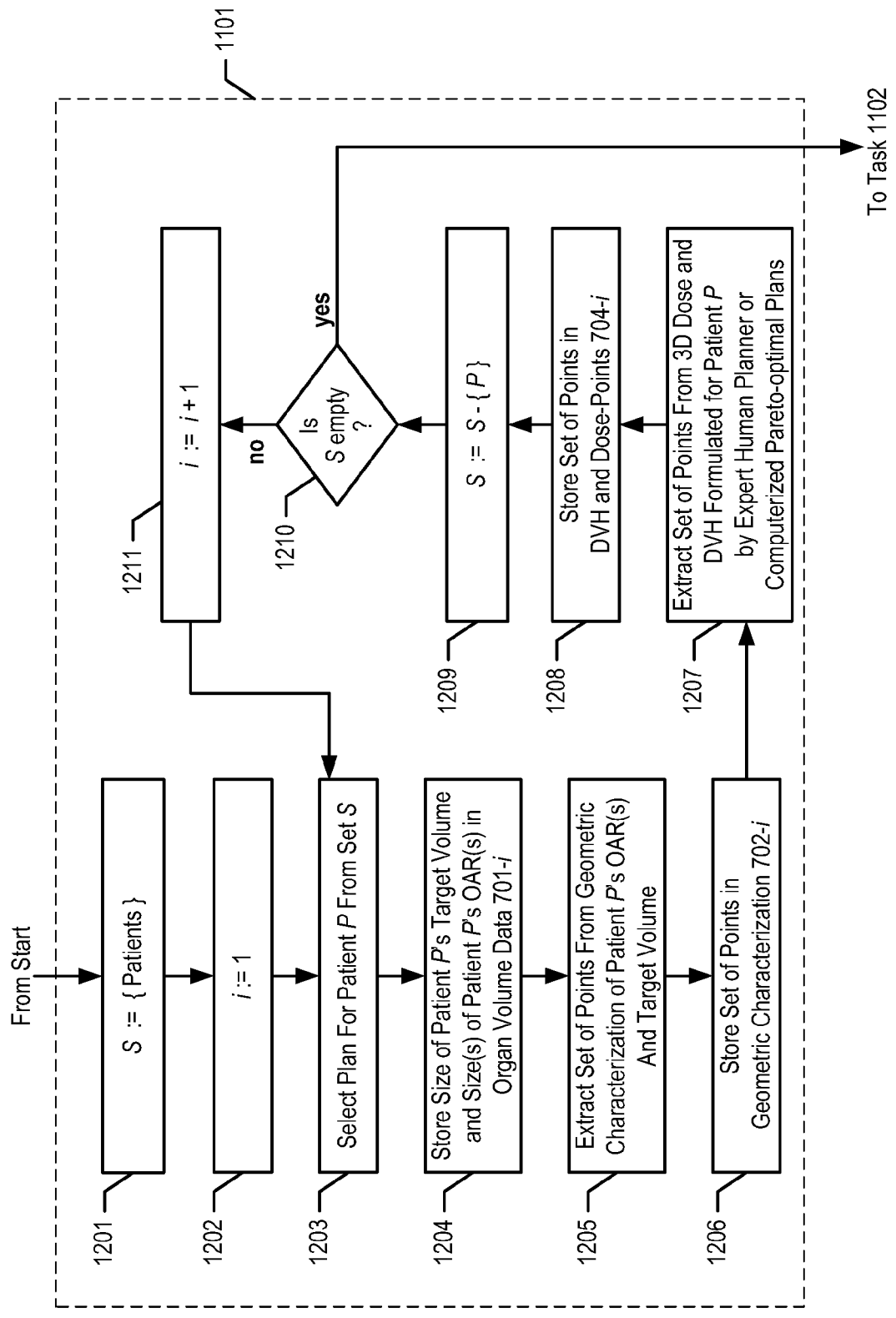
FIG. 12 depicts a detailed flowchart of task 1101, as shown in FIG. 11, in accordance with the illustrative embodiment of the present invention.

FIG. 12 depicts a detailed flowchart of task 1101, in accordance with the illustrative embodiment of the present invention. It will be clear to those skilled in the art, after reading this disclosure, which subtasks depicted in FIG. 12 can be performed simultaneously or in a different order than that depicted.

At subtask 1201, data-processing system 401 initializes variable S to a set of radiation treatment plans previously formulated by expert human planners using trial-and-error approach or pareto-front guided search.

At subtask 1202, data-processing system 401 initializes variable i to 1.

At subtask 1203, data-processing system 401 selects from set S a plan for a patient P.

At subtask 1204, data-processing system 401 stores the size of patient P's target volume and the size(s) of patient P's organ(s) at risk in organ volume data 701-$i$ of patient record 601-$i$ in plan database 402.

At subtask 1205, data-processing system 401 extracts a set of points from a geometric characterization of patient P's organ(s) at risk and his or her target volume.

At subtask 1206, data-processing system 401 stores the set of points obtained at subtask 1205 in geometric characterization 702-$i$ of patient record 601-$i$ in plan database 402.

At subtask 1207, data-processing system 401 extracts a set of points from a dose volume histogram and dose points meeting other specific geometric characteristics that were formulated for patient P by either an expert human planner or computerized pareto-optimal plans.

At subtask 1208, data-processing system 401 stores the set of points obtained at subtask 1207 in dose volume histogram 703-$i$ of patient record 601-$i$ in plan database 402.

At subtask 1209, data-processing system 401 removes patient P from set S.

At subtask 1210, data-processing system 401 checks whether set S is empty; if so, execution continues at task 1102 of FIG. 11, otherwise execution proceeds to subtask 1210.

At subtask 1211, data-processing system 401 increments variable i. After subtask 1210, execution continues back at subtask 1203.

Figure 13:
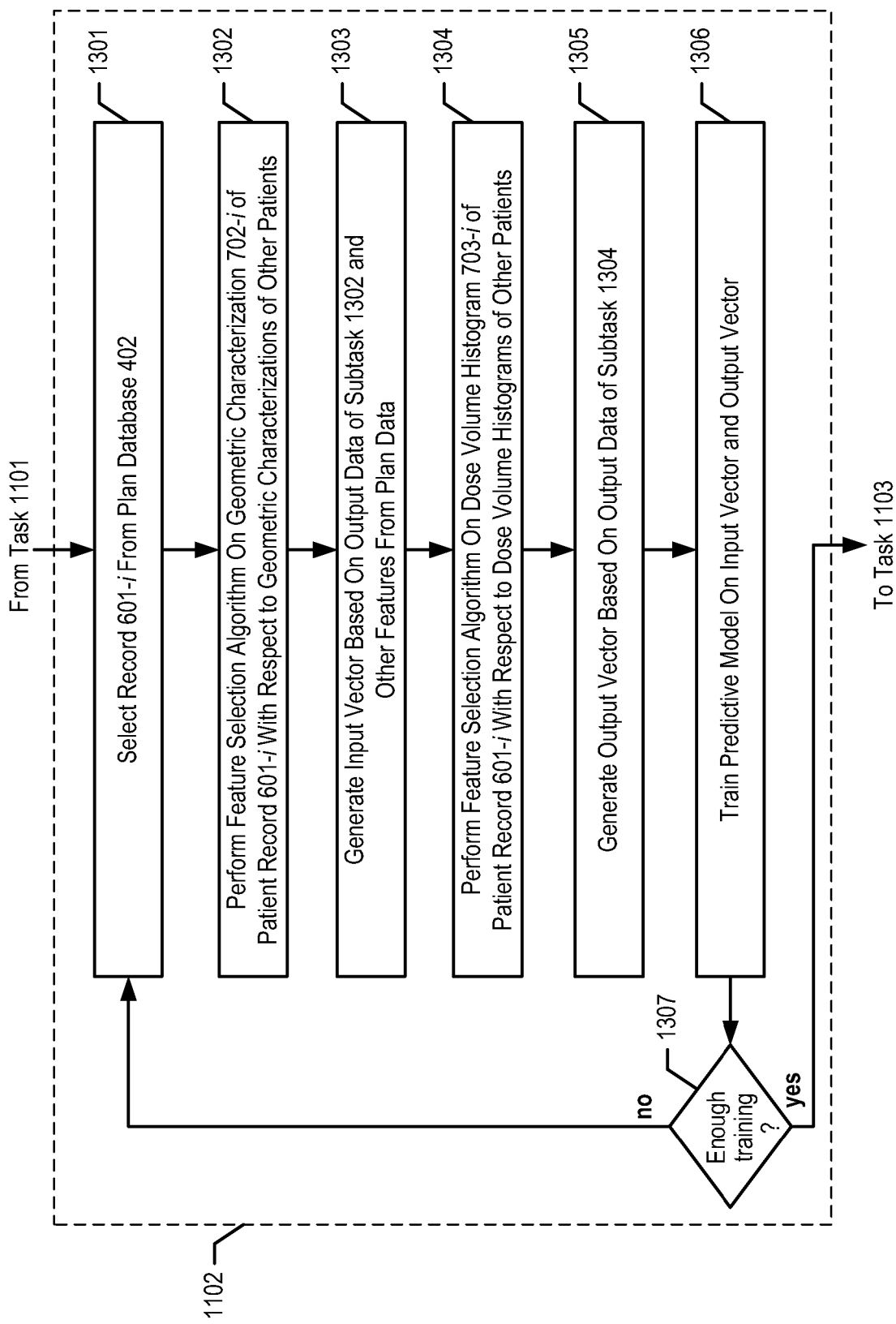
FIG. 13 depicts a detailed flowchart of task 1102, as shown in FIG. 11, in accordance with the illustrative embodiment of the present invention.

FIG. 13 depicts a detailed flowchart of task 1102, in accordance with the illustrative embodiment of the present invention. It will be clear to those skilled in the art, after reading this disclosure, which subtasks depicted in FIG. 13 can be performed simultaneously or in a different order than that depicted.

At subtask 1301, data-processing system 401 selects some record 601-$i$ from plan database 402, where i is an integer between 1 and D inclusive.

At subtask 1302, data-processing system 401 performs a feature selection algorithm on geometric characterization 702-$i$ of patient record 601-$i$ with respect to the geometric characterizations of other patients. In accordance with the illustrative embodiment, a principal component analysis is employed as the feature selection algorithm at subtask 1302; however, as will be appreciated by those skilled in the art, in some other embodiments of the present invention some other type of feature selection algorithm might be employed at subtask 1302, and it will be clear to those skilled in the art, after reading this disclosure, how to make and use embodiments of the present invention that employ such alternative feature selection algorithms.

Subtask 1302 is described in detail below and with respect to FIG. 14.

At subtask 1303, data-processing system 401 generates an input vector that comprises (i) one or more values based on the output data of the principal component analysis of subtask 1302, (ii) target size 801-$i$ of patient record 601-$i$, and (iii) and organ at risk (OAR) sizes 802-$i$-1 through 802-$i$-R of patient record 601-$i$. As will be appreciated by those skilled in the art, in some embodiments of the present invention the one or more values of item (i) might simply be the principal component scores corresponding to the M eigenvalues obtained at subtask 1302, while in some other embodiments the one or more values of item (i) might be derived in some way from these M eigenvalues (e.g., via normalization of the eigenvalues, via a technique that combines the eigenvalues in some fashion, etc.).

At subtask 1304, data-processing system 401 performs a feature selection algorithm on:
(i) dose volume histogram 703-$i$ of patient record 601-$i$, and
(ii) dose points meeting other specific geometric characteristics with respect to the dose volume histograms of other patients. In accordance with the illustrative embodiment, a principal component analysis is employed as the feature selection algorithm at subtask 1304; however, as will be appreciated by those skilled in the art, in some other embodiments of the present invention some other type of feature reduction algorithm might be employed at subtask 1304, and it will be clear to those skilled in the art, after reading this disclosure, how to make and use embodiments of the present invention that employ such alternative feature selection algorithms.

Subtask 1304 is performed in a manner similar to subtask 1302, and is described in detail below and with respect to FIG. 15.

At subtask 1305, data-processing system 401 generates an output vector that is based on the output data of the principal component analysis of subtask 1304. As will be appreciated by those skilled in the art, in some embodiments of the present invention the output vector might simply contain principal component scores corresponding to the Q eigenvalues obtained at subtask 1304, while in some other embodiments the output vector might be derived in some way from these Q eigenvalues (e.g., via normalization of the eigenvalues, via a technique that combines the eigenvalues in some fashion, etc.).

At subtask 1306, data-processing system 401 trains the predictive model on the input vector and output vector generated at subtasks 1303 and 1305, respectively.

At subtask 1307, data-processing system 401 determines whether the predictive model has been trained sufficiently. As will be appreciated by those skilled in the art, in some embodiments of the present invention this determination might be based on one or more convergence criteria, while in some other embodiments of the present invention the determination might be made in some other fashion (e.g., based on some other criteria, based on a pre-determined number of iterations, etc.).

If the determination at subtask 1307 is negative, execution continues back at subtask 1301; otherwise, execution proceeds to task 1103 of FIG. 11.

Figure 14:
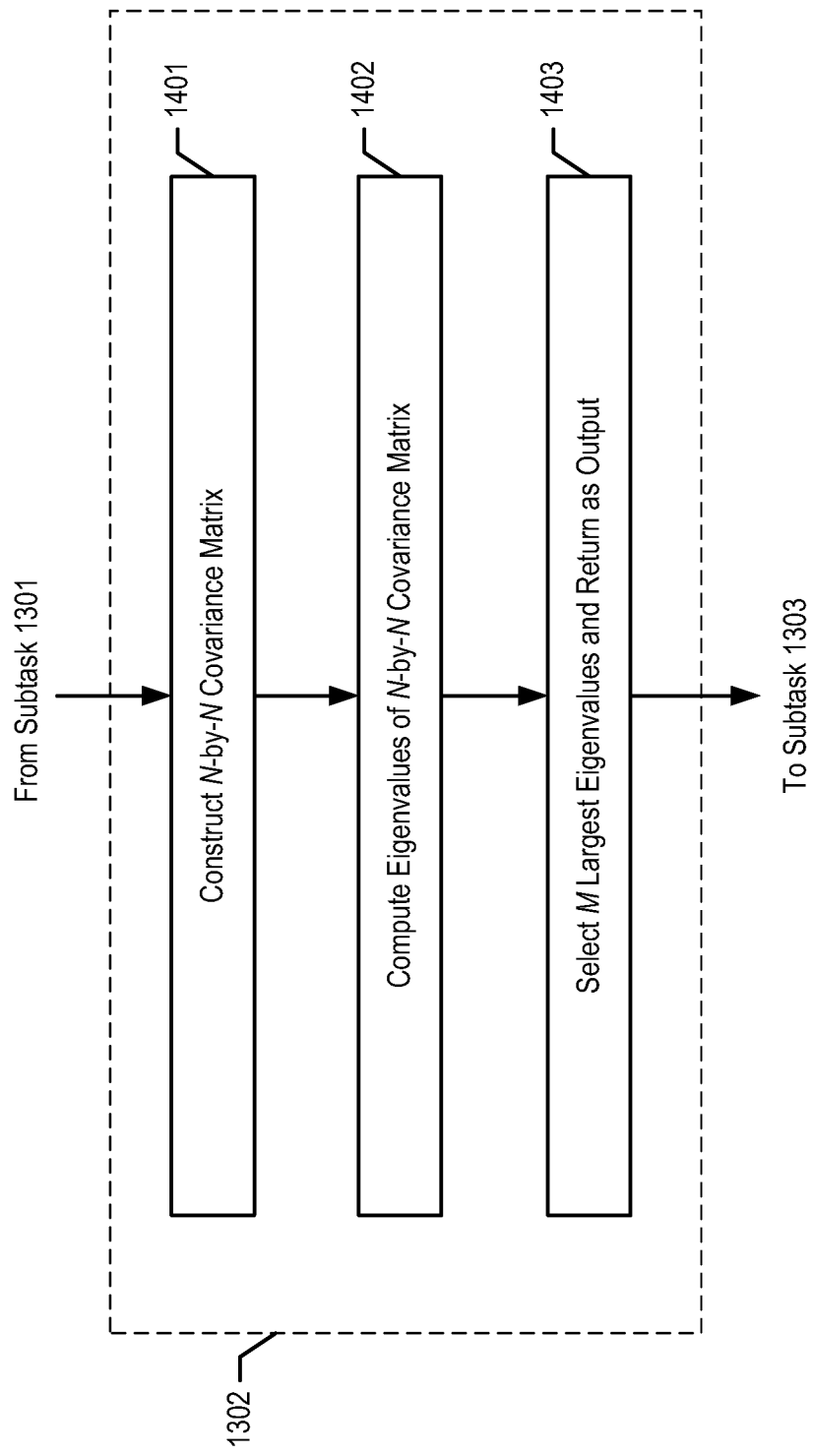
FIG. 14 depicts a detailed flowchart of subtask 1302, as shown in FIG. 13, in accordance with the illustrative embodiment of the present invention.

FIG. 14 depicts a detailed flowchart of subtask 1302, in accordance with the illustrative embodiment of the present invention. As noted above, in accordance with the illustrative embodiment, a principal component analysis is employed as the feature selection algorithm in the subtasks of FIG. 14; however, as will be appreciated by those skilled in the art, in some other embodiments of the present invention some other type of feature selection algorithm might be employed, and it will be clear to those skilled in the art, after reading this disclosure, how to make and use embodiments of the present invention that employ such alternative feature selection algorithms. It will further be clear to those skilled in the art, after reading this disclosure, which subtasks depicted in FIG. 14 can be performed simultaneously or in a different order than that depicted.

At subtask 1401, data-processing system 401 constructs an N-by-N covariance matrix of all feature points across all training plans, in well known fashion, where N is a positive integer equal to K.

At subtask 1402, data-processing system 401 computes the eigenvalues of the N-by-N covariance matrix, in well-known fashion.

At subtask 1403, data-processing system 401 selects the M largest of the eigenvalues computed at subtask 1402, where M is a positive integer between 1 and N inclusive, and returns the principal component scores associated with selected eigenvalues as outputs to subtask 1303 of FIG. 13. After subtask 1403, execution continues at subtask 1303.

Figure 15:
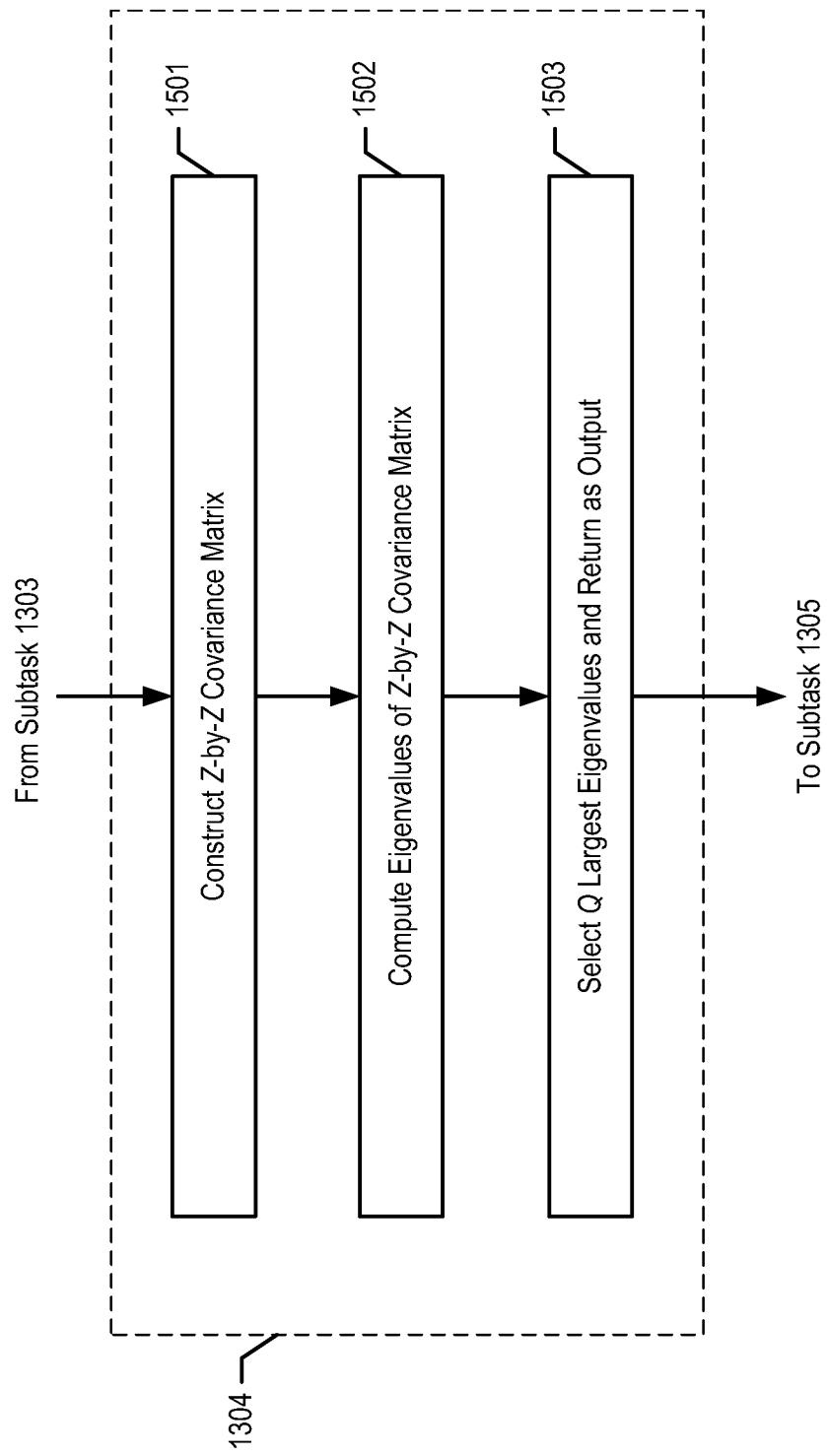
FIG. 15 depicts a detailed flowchart of subtask 1304, as shown in FIG. 13, in accordance with the illustrative embodiment of the present invention.

FIG. 15 depicts a detailed flowchart of subtask 1304, in accordance with the illustrative embodiment of the present invention. As noted above, in accordance with the illustrative embodiment, a principal component analysis is employed as the feature reduction algorithm in the subtasks of FIG. 15; however, as will be appreciated by those skilled in the art, in some other embodiments of the present invention some other type of feature reduction algorithm might be employed, and it will be clear to those skilled in the art, after reading this disclosure, how to make and use embodiments of the present invention that employ such alternative feature reduction algorithms. It will further be clear to those skilled in the art, after reading this disclosure, which subtasks depicted in FIG. 15 can be performed simultaneously or in a different order than that depicted.

At subtask 1501, data-processing system 401 constructs a Z-by-Z covariance matrix of Z sample points of dose volume histograms across all plans, in well known fashion, where Z is a positive integer equal to L. As will be appreciated by those skilled in the art, in some embodiments of the present invention the value of Z might be the same as the value of N used at subtask 1401, while in some other embodiments of the present invention, Z might have a different value than N.

At subtask 1502, data-processing system 401 computes the eigenvalues of the Z-by Z covariance matrix, in well-known fashion.

At subtask 1503, data-processing system 401 selects the Q largest of the eigenvalues computed at subtask 1502, where Q is a positive integer between 1 and Z inclusive, and returns the principal component scores associated with the selected eigenvalues as outputs to subtask 1305 of FIG. 13. After subtask 1503, execution continues at subtask 1305.

Figure 16:
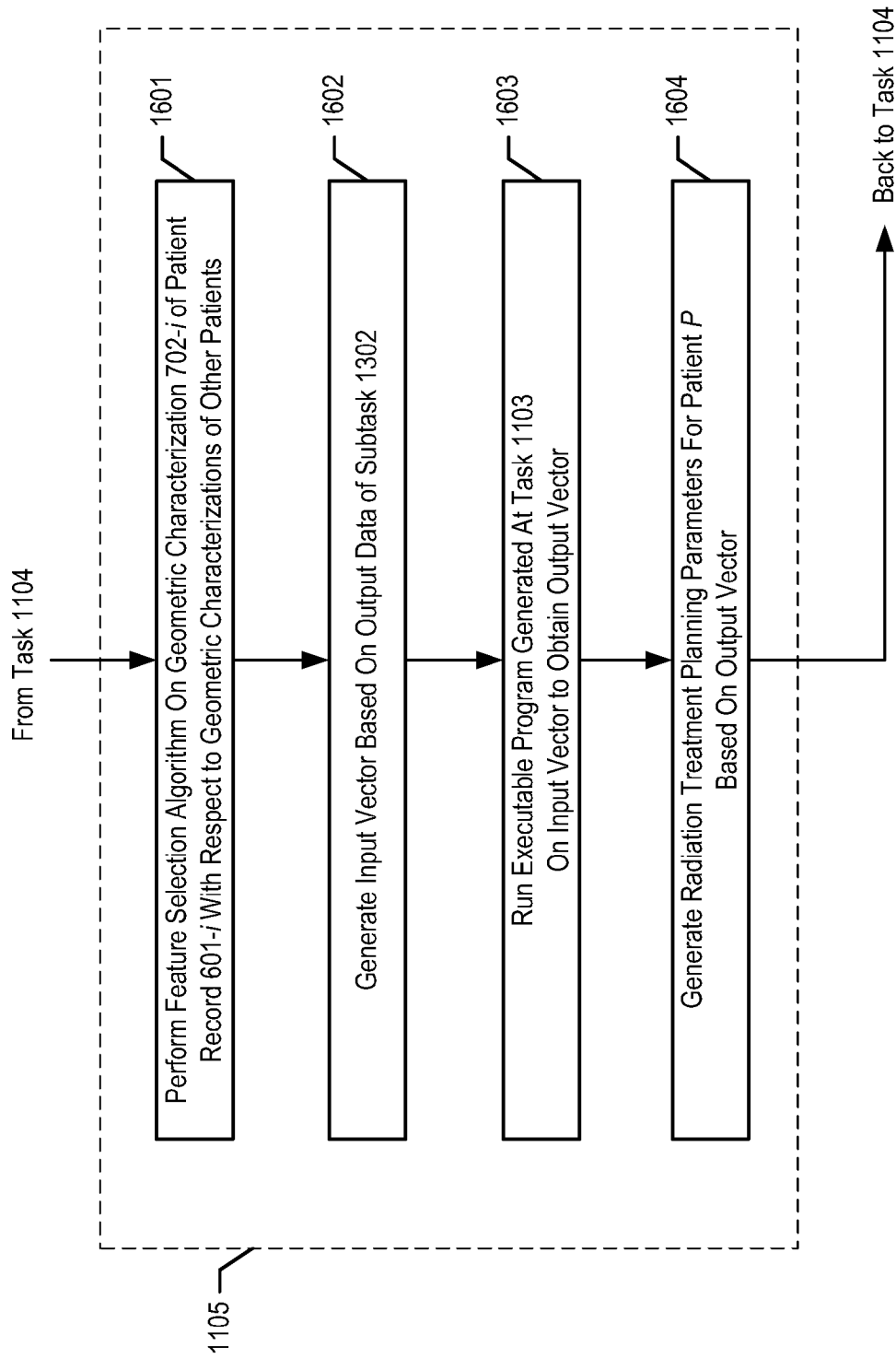
FIG. 16 depicts a detailed flowchart of task 1105, as shown in FIG. 11, in accordance with the illustrative embodiment of the present invention.

FIG. 16 depicts a detailed flowchart of task 1105, in accordance with the illustrative embodiment of the present invention. It will be clear to those skilled in the art, after reading this disclosure, which subtasks depicted in FIG. 16 can be performed simultaneously or in a different order than that depicted.

At subtask 1601, data-processing system 401 performs a feature selection algorithm on the geometric characterization 702-$i$ for patient P (received at task 1104) with respect to the geometric characterizations of other patients. As noted above, in accordance with the illustrative embodiment, a principal component analysis is employed as the feature selection algorithm in the subtasks of FIG. 16; however, as will be appreciated by those skilled in the art, in some other embodiments of the present invention some other type of feature selection algorithm might be employed, and it will be clear to those skilled in the art, after reading this disclosure, how to make and use embodiments of the present invention that employ such alternative feature selection algorithms.

Subtask 1601 is described in detail below and with respect to FIG. 17.

At subtask 1602, data-processing system 401 generates an input vector that contains (i) one or more values based on the output data of the principal component analysis of subtask 1601, (ii) the size and shape of patient P's target volume, and (iii) the size(s) and shape(s) of patient P's organ(s) at risk. As will be appreciated by those skilled in the art, in some embodiments of the present invention the one or more values of item (i) might simply be the principal component scores corresponding to the M eigenvalues obtained at subtask 1601, while in some other embodiments the one or more values of item (i) might be derived in some way from these M eigenvalues (e.g., via normalization of the eigenvalues, via a technique that combines the eigenvalues in some fashion, etc.).

At subtask 1603, data-processing system 401 runs the executable program generated at task 1103 on the input vector and obtains an output vector.

At subtask 1604, data-processing system 401 generates radiation treatment planning parameters for patient P based on the output vector. Subtask 1604 is described in detail below and with respect to FIG. 18.

After subtask 1604, execution continues back at task 1104.

Figure 17:
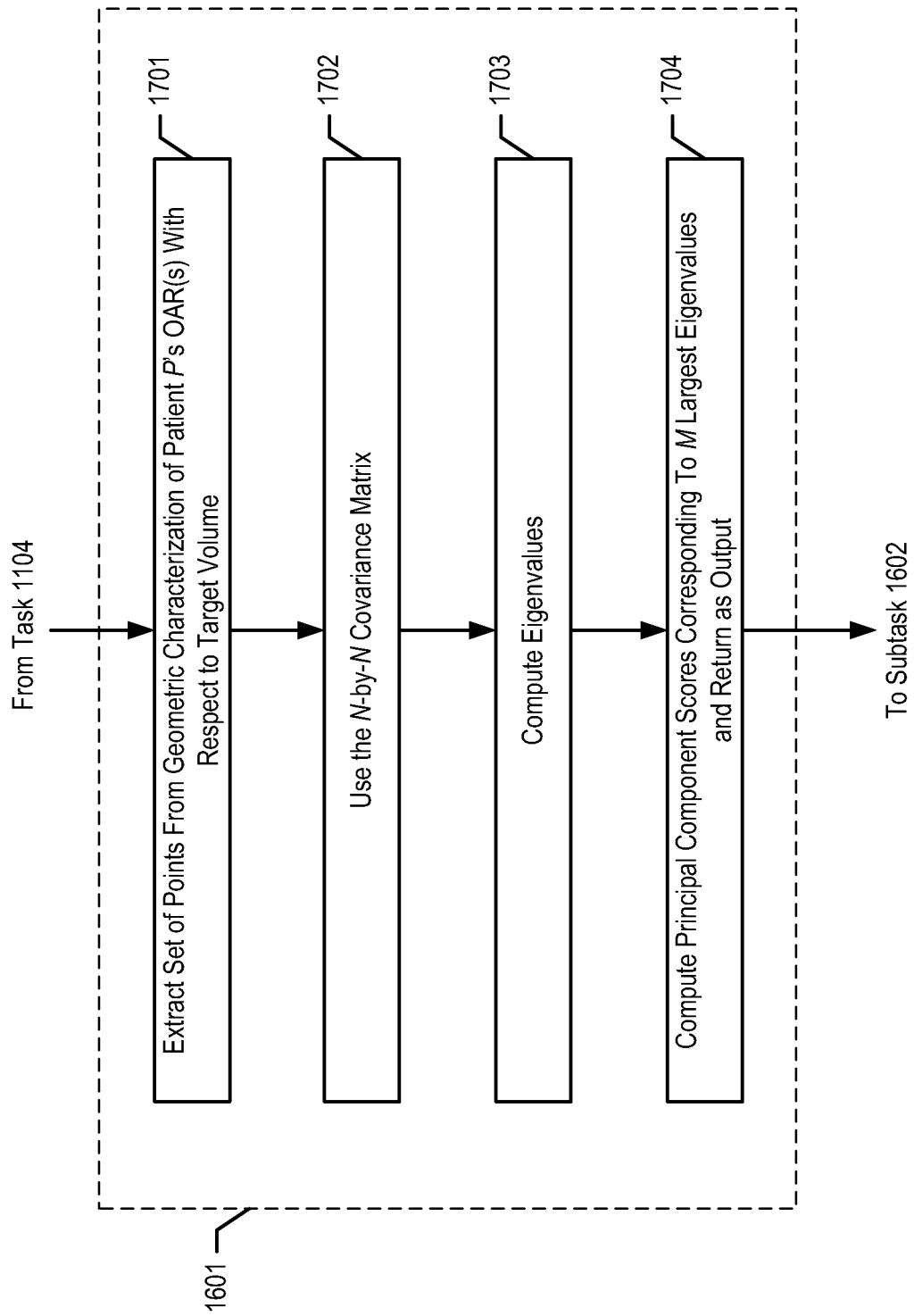
FIG. 17 depicts a detailed flowchart of subtask 1601, as shown in FIG. 16, in accordance with the illustrative embodiment of the present invention.

FIG. 17 depicts a detailed flowchart of subtask 1601, in accordance with the illustrative embodiment of the present invention. As noted above, in accordance with the illustrative embodiment, a principal component analysis is employed as the feature selection algorithm in the subtasks of FIG. 17; however, as will be appreciated by those skilled in the art, in some other embodiments of the present invention some other type of feature selection algorithm might be employed, and it will be clear to those skilled in the art, after reading this disclosure, how to make and use embodiments of the present invention that employ such alternative feature selection algorithms. It will further be clear to those skilled in the art, after reading this disclosure, which subtasks depicted in FIG. 17 can be performed simultaneously or in a different order than that depicted.

At subtask 1701, data-processing system 401 extracts a set of N points from the geometric characterization for patient P.

At subtask 1702, data-processing system 401 uses the N-by-N covariance matrix, in well known fashion.

At subtask 1703, data-processing system 401 computes the eigenvalues, in well-known fashion.

At subtask 1704, data-processing system 401 computes the principal component scores corresponding to the M largest of the eigenvalues computed at subtask 1603 and returns the principal component scores as outputs to subtask 1602 of FIG. 16. After subtask 1704, execution continues at subtask 1602.

Figure 18:
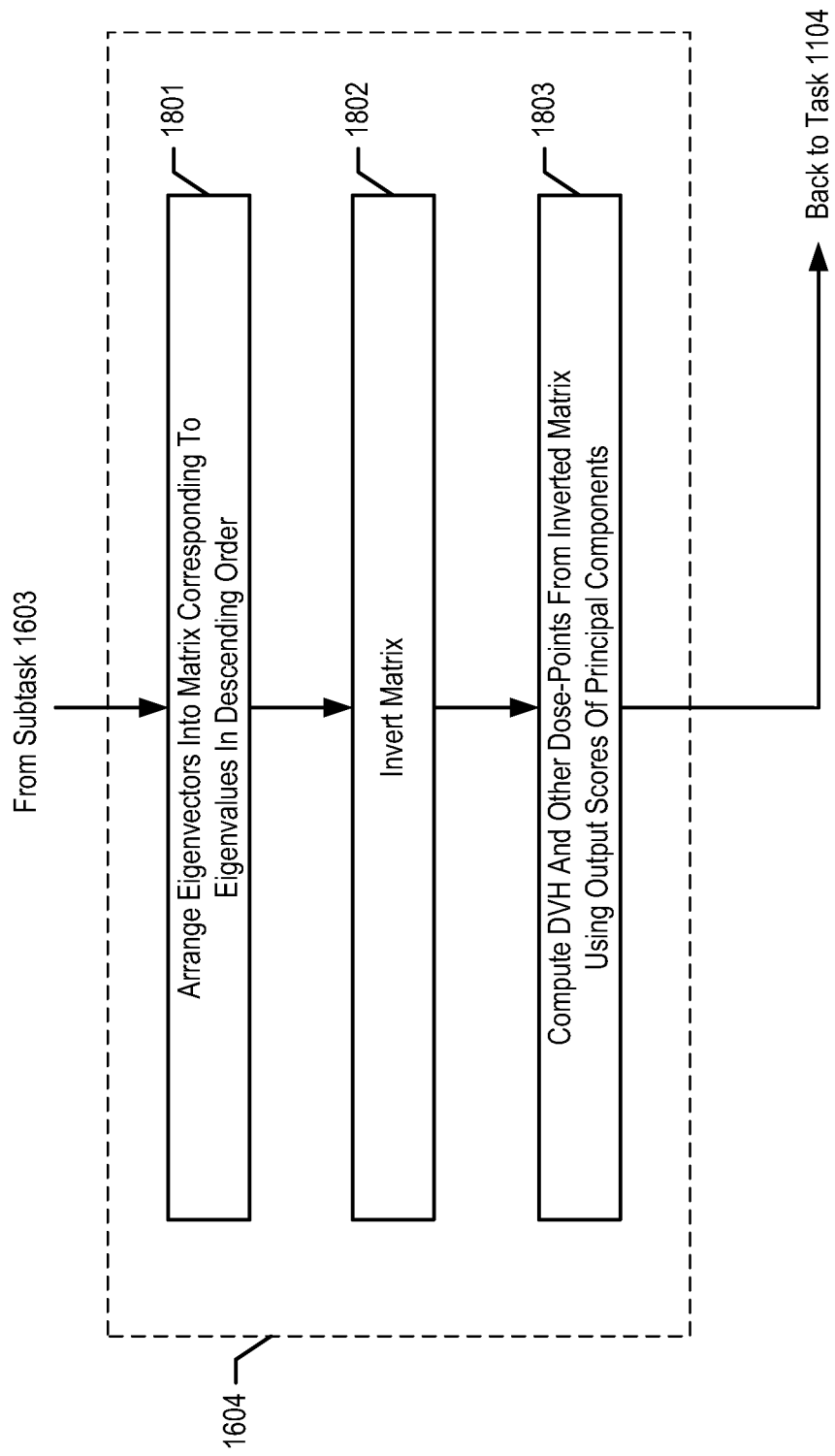
FIG. 18 depicts a detailed flowchart of subtask 1604, as shown in FIG. 16, in accordance with the illustrative embodiment of the present invention.

FIG. 18 depicts a detailed flowchart of subtask 1604, in accordance with the illustrative embodiment of the present invention. As noted above, in accordance with the illustrative embodiment, a principal component analysis is employed as the feature selection algorithm in the subtasks of FIG. 18; however, as will be appreciated by those skilled in the art, in some other embodiments of the present invention some other type of feature selection algorithm might be employed, and it will be clear to those skilled in the art, after reading this disclosure, how to make and use embodiments of the present invention that employ such alternative feature selection algorithms. It will further be clear to those skilled in the art, after reading this disclosure, which subtasks depicted in FIG. 18 can be performed simultaneously or in a different order than that depicted.

At subtask 1801, data-processing system 401 arranges the eigenvectors computed at subtask 1704 into a matrix that corresponds to the eigenvalues in descending order.

At subtask 1802, data-processing system 401 inverts the matrix constructed at subtask 1801, in well-known fashion.

At subtask 1803, data-processing system 401 computes a dose volume histogram (DVH) and other dose-points from the inverted matrix using the output scores of the principal components.

After subtask 1803, execution continues back at task 1104.

As will be appreciated by those skilled in the art, although the illustrative embodiment is disclosed in the context of a single target volume, the techniques of the illustrative embodiment can easily be adapted by one skilled in the art to accommodate patients having a plurality of target volumes.

As will further be appreciated by those skilled in the art, although the illustrative embodiment employs principal component analysis as the feature selection algorithm, some other embodiments of the present invention might employ some other type of feature selection algorithm, and it will be clear to those skilled in the art, after reading this disclosure, how to make and use such alternative embodiments.

As will yet further be appreciated by those skilled in the art, although the geometric characterizations of the illustrative embodiment may be expressed as distances in Euclidean space, the distances are in fact general measurements that may be expressed in some other type of space (e.g., a distance space distorted by radiation beam geometry, etc.), and it will be clear to those skilled in the art, after reading this disclosure, how to make and use embodiments that employ such alternative distance spaces.

As will still further be appreciated by those skilled in the art, although the illustrative embodiment is disclosed in the context of general intensity-modulated radiation therapy (IMRT), the techniques of the illustrative embodiment can be employed for both static gantry angle intensity-modulated radiation therapy (IMRT) and rotation gantry volumetric modulated arc therapy (VMAT), as well as other types of radiation therapy.

It is to be understood that the disclosure teaches just one example of the illustrative embodiment and that many variations of the invention can easily be devised by those skilled in the art after reading this disclosure and that the scope of the present invention is to be determined by the following claims.

What is claimed is:

1. A method comprising:
receiving by a data-processing system:
(a) first data based on a geometric characterization of one or more organs at risk proximate to a target volume of a patient P, wherein the geometric characterization associates each of a plurality of distances from the target volume with a respective percentage of the volume of the one or more organs at risk;
(b) second data comprising a size of the target volume and the respective sizes and shapes of the one or more organs at risk; and
generating, by said data-processing system using a predictive model, one or more radiation treatment planning parameters for said patient P based on the first data and the second data.

2. The method of claim 1, wherein said one or more radiation treatment planning parameters are represented by at least one of a dose distribution and a dose volume histogram.

3. The method of claim 1 further comprising receiving by a data processing system third data based on a geometric characterization of said target volume with respect to said one or more organs at risk.

4. The method of claim 1 wherein the first data and the second data are derived via a feature selection algorithm that is applied to a larger set of data that represent geometric characterizations of one or more organs at risk proximate to a target volume.

5. The method of claim 4 wherein said feature selection algorithm comprises a principal component analysis, and wherein said principal component analysis is based on an N-by-N covariance matrix, and wherein N is a positive integer greater than one.

6. The method of claim 5 wherein the first data and the second data are based on the M largest eigenvalues of said covariance matrix, and wherein M is a positive integer between 1 and N inclusive.

7. The method of claim 1 and further wherein said predictive model has been trained on a set of input-output pairs, and wherein the output of each input-output pair is based on a dose distribution and a dose volume histogram for a respective patient, and wherein the input of each input-output pair comprises one or more data that are based on the geometric characterization for said respective patient.

8. A method comprising training by a data-processing system a predictive model on a plurality of input-output mappings, wherein the output of each input-output mapping is based on a dose distribution and a dose volume histogram for a respective patient, and wherein the input of each input-output mapping comprises one or more data that are based on a geometric characterization of one or more organs at risk proximate to a target volume of the respective patient, wherein said geometric characterization associates each of a plurality of distances from said target volume with a respective percentage of the volume of said one or more organs at risk.

9. The method of claim 8 further comprising generating a computer-executable program based on the trained predictive model.

10. The method of claim 8 wherein said one or more data also comprises the size of one or more partial volumes.

11. The method of claim 8 wherein said geometric characterization associates a three-dimensional point in said target and one or more organs at risk with a set of values that represent the unique relationship between the point and the target and the organs at risk.

12. The method of claim 8 wherein the output of each input-output mapping is derived via a feature selection algorithm that is applied to dose volume histograms for a plurality of patients.

13. The method of claim 12 wherein said feature selection algorithm comprises a principal component analysis, and wherein said principal component analysis is based on an Z by Z covariance matrix, and wherein Z is the plurality of points from a dose volume histogram for a respective patient, and wherein Z is a positive integer greater than one.

14. The method of claim 13 wherein the output of an input-output mapping comprises the Q largest eigenvalues of said covariance matrix, and wherein Q is a positive integer between 1 and Z inclusive.

15. A method comprising storing in a database, by a data-processing system:
(a) one or more planning parameters of a first radiation treatment plan, wherein said first radiation treatment plan is for a first patient and is generated by one of:
  (i) an expert human planner, and
  (ii) a data-processing system using one or both of multi-objective optimization and pareto front search;
(b) a first geometric characterization of a first non-empty set of organs at risk proximate to a first target volume of said first patient, wherein the first geometric characterization is a function of volume for the organs at risk;
(c) one or more planning parameters of a second radiation treatment plan, wherein said second radiation treatment plan is for a second patient and is generated by one of:
  (i) an expert human planner, and
  (ii) a data-processing system using one or both of multi-objective optimization and pareto front search; and
(d) a second geometric characterization of a second non-empty set of organs at risk proximate to a second target volume of said second patient, wherein the second geometric characterization is a function of volume for the organs at risk.

16. The method of claim 15 further comprising:
generating by said data-processing system:
(i) a first input-output mapping based on said first geometric characterization and on said one or more planning parameters of said first radiation treatment plan, and
(ii) a second input-output mapping based on said second geometric characterization and on said one or more planning parameters of said second radiation treatment plan; and
training by said data-processing system a predictive model on said first input-output mapping and said second input-output mapping.

17. A method comprising:
receiving by a data-processing system one or more data, wherein at least one of the data is based on a geometric characterization of one or more organs at risk proximate to a target volume of a patient P, and wherein the geometric characterization associates each of a plurality of distances from said target volume with a respective percentage of the volume of said one or more organs at risk; and
generating by the data-processing system one or more radiation treatment planning parameters for the patient P based on the one or more data.

18. A method comprising:
receiving first data and second data at a data-processing system, wherein:
(a) the first data is based on a geometric characterization of one or more organs at risk proximate to a target volume of a patient P; and
(b) the second data is based on the size of the target volume and the respective sizes and shapes of the one or more organs at risk; and
generating by the data-processing system one or more radiation treatment planning parameters for the patient P based on the first data and the second data.

* * * * *